United States Patent [19]
Parham et al.

[11] Patent Number: 4,794,090
[45] Date of Patent: Dec. 27, 1988

[54] IMMOBILIZATION SUPPORT FOR BIOLOGICALS

[75] Inventors: Marc E. Parham, Bedford; Julie L. Rudolph, Carlisle, both of Mass.

[73] Assignee: W. R. Grace & Co.-Conn., New York, N.Y.

[21] Appl. No.: 911,944

[22] Filed: Sep. 26, 1986

[51] Int. Cl.$^4$ .................. G01N 33/545; G01N 33/549
[52] U.S. Cl. .......................................... 436/531; 435/7; 436/524; 436/527; 436/530; 436/532; 436/534; 436/548; 436/809; 436/824; 428/423.1
[58] Field of Search .................... 435/7; 436/524, 527, 436/530, 531, 532, 534, 548, 809, 824

[56] References Cited

U.S. PATENT DOCUMENTS

| | | |
|---|---|---|
| 4,137,200 | 1/1979 | Wood et al. . |
| 4,195,127 | 3/1980 | Hartdegen et al. .............. 436/535 X |
| 4,342,739 | 8/1982 | Kakimi et al. ........................ 424/1.1 |
| 4,378,435 | 3/1983 | Takagi et al. . |
| 4,450,231 | 5/1984 | Ozkan ............................. 436/531 X |
| 4,483,928 | 11/1984 | Suzuta et al. .................... 436/520 X |
| 4,610,962 | 9/1986 | Takagi et al. . |
| 4,632,901 | 12/1986 | Valkirs et al. ................... 436/513 X |

OTHER PUBLICATIONS

Sostero et al.,—"Immobilization on Nylon Beads of Anti Australia Antigen Antibodies Application to a Hepatitis B Surface Antigen Immuno Enzyme Assay'-'—Servizio Enzimologia—60/508-12—1981 (abstract only).

Kumakura et al.,—"Sheets Obtained by Radiation Polymerization for Enzyme Immunoassay"—Int. J. Appl. Radiat. Isot.—35/471-4—1984 (abstract only).

Primary Examiner—Robert J. Warden
Assistant Examiner—Richard Wagner
Attorney, Agent, or Firm—Jill H. Krafte

[57] ABSTRACT

A diagnostic assay support matrix is prepared by coating a support matrix with a polymer resistant to nonspecific protein binding and immobilizing the desired biologically active agent on the polymer surface.

20 Claims, No Drawings

IMMOBILIZATION SUPPORT FOR BIOLOGICALS

BACKGROUND OF THE INVENTION

This invention relates to the field of immobilized biologicals for use in diagnostics or other analytical testing. More specifically, it has been found that the application of certain polymeric coatings onto microporous support matrices provides two advantages of major significance to this art. First, it simplifies the procedures required for immobilizing the biological onto the membrane. Second, it essentially eliminates nonspecific binding of protein ont the support surface. Diagnostic assays typically utilize a microporous matrix as a support for a bioaffinity agent, which detects the presence of a particular desired protein (the "target" protein). These bioaffinity agents, usually antibodies to the target protein, are immobilized in some manner on the matrix to yield an "assay matrix" which is used in the diagnostic testing.

Diagnostic membranes are conventionally prepared from microporous membranes, such as nylon, in the following manner. A solution containing the bioaffinity agent is dotted onto the membrane and dried, becoming immobilized on the membrane by passive adsorption. Next, a blocking step is required for the prevention of nonspecific binding of either the target protein or a recognition protein or agent to the target protein. Nonspecific binding across the entire membrane renders the assay inaccurate and unreadable. The blocking step conventionally comprises thoroughly coating the membrane with a protein in order to fill, or block, the nonspecific binding sites available on the support surface.

The assay typically is conducted by passing test fluid through the membrane. If the target protein is present in the test fluid, it will bind to a unique binding site of the primary antibody immobilized on the membrane. The membrane then is treated with a recognition conjugate, consisting of a recognition antibody (which binds to a second binding site on the target protein) coupled to an enzyme, such as horseradish peroxidase, which can be induced to generate a color change under positive test conditions. The membrane is rinsed and treated with a substrate for the enzyme-mediated color change reaction. If the target protein was present in the test fluid, it will have become bound to the primary antibody and, in turn, will have bound the recognition conjugate. The enzyme portion of the recognition conjugate will react with the substrate, producing an easily detected color change for a positive assay. If the protein was not present, the recognition conjugate will not be bound to the membranes and no color change will occur upon treatment with the substrate.

It can be seen that the occurance of nonspecific binding of proteins will seriously impair the usefulness of diagnostic assays of this type. Untreated microporous membranes or particulate support matrices display a strong propensity to adsorb proteins on contact. Thus, any protein present in the test fluid would be adsorbed over the whole support, rather than just being bound to the primary antibody. It is preferred to have an assay system in which a positive result is readily and clearly detectable as a sharp colored dot or pattern on a contrasting background.

Even more detrimental to this assay technique is nonspecific adsorption of the recognition conjugate. The utility of the assay depends upon the recognition conjugate binding only to the target protein, which has been bound by the immobilized primary antibody. If the recognition conjugate can be adsorbed directly onto the support itself, false positives or blinding of the results by a color change over the whole support surface will occur, rendering the assay useless.

SUMMARY OF THE INVENTION

A protein non-adsorptive microporous support matrix is created by application and polymerization of a prepolymer selected from a class characterized by the resistance of the polymer to nonspecific protein binding. The desired biologically active agent can be easily immobilized on the treated surface and the assay support may be used in a diagnostic assay without further processing to prevent the complications of nonspecific protein binding as discussed above.

It is a primary object of this invention to provide for use in diagnostic assays an improved microporous support matrix to which a bioaffinity agent such as an antibody can be readily immobilized.

This invention is further intended to streamline and simplify the manufacturing procedures for preparing assay supports. Use of the improved assay support of this invention completely eliminates the protein blocking steps required by conventional methods.

It is a related object to minimize the quantity of bioaffinity agent required per assay by providing an improved support matrix and a method of immobilization which causes minimal loss of biological activity.

This invention also is intended to improve reliability of diagnostic assays by significantly reducing susceptibility to false results or to blinding of results due to nonspecific protein adsorption. The assays of this invention retain a white background during the test protocol which is advantageous for clear distinction between positive and negative results. Moreover, it is intended to provide an assay support matrix which resists deterioration upon exposure to air or moisture.

It is a further object to provide an assay system in which a positive result is apparent substantially instantaneously as a visually detectable color change, thereby eliminating the waiting time necessary with conventional assays.

DETAILED DESCRIPTION OF THE INVENTION

The improved support matrix of this invention is characterized by a polymeric coating which simultaneously facilitates the immobilization of the desired bioaffinity agent and resists interference with the assay by the nonspecific binding of protein. The assay support may be in the form of a microporous or nonwoven membrane, particulate porous or nonporous media suitable for use in diagnostic assays, or a nonporous device such as a microtiter plate.

Microporous materials such as those now utilized for diagnostics will be suitable. Nylon membranes are frequently used. Alternatively, membranes o polypropylene, various polyesters, polyvinyl fluoride, Teflon (TM, E. I. DuPont de Nemours & Co.) or cellulose may be used. Membranes of woven or nonwoven materials may be of suitable surface area such that the test fluid and any solutes contained therein will wet the surface and may or may not pass through the support. Membranes with pore sizes of about 0.05 or less to about 5.0 microns or greater are typically used. The membrane material must be insoluble in the solvents used both in preparing the assay support matrix and in conducting the assay itself.

Alternatively, porous or nonporous particulate support matrices may be used. For example, silica gel and either inorganic or organic beaded matrices would be suitable. The particle size will be chosen according to the format in which the assay support matrix will be used. For example, if the matrix will be in a column or packed bed configuration, the particles must be of sufficient size to allow flow of the test fluid and reagent solutions through the bed. One micron beads may be desirable for use in this embodiment. Again, the material chosen must be insoluble in the solvents used in preparing the matrix and conducting the assay.

In another alternative embodiment, the support matrix may be a nonporous assay device, such as a microtiter plate. Devices such as this typically are composed of materials such as polystyrene, polypropylene, polyvinylchloride and the like. Care should be taken in preparing assay support of matrices of this embodiment either to select solvents which will not compromise the integrity of the support, or to quickly remove the solvent after the coating step before the support can be eroded or otherwise damaged.

The selected membrane or other support matrix is first treated to provide a polymer coating which confers resistance to nonspecific protein binding. Polyurethane polymers with the desired ability to resist nonspecific protein adsorption are used. The support matrix is coated with the polyurethane prepolymer in a volatile organic solvent solution, as described below in more detail.

The polyurethane prepolymers used in the invention may be prepared by capping a polyoxyalkylene polyol with a polyisocyanate compound, such that the capped product (the prepolymer) has a reaction functionality greater than two. Complete end capping of the polyol is desired. The polyols used to prepare the prepolymer may have an average molecular weight in the range of about 200 to about 20,000. It may be preferred to use a prepolymer substantially or exclusively comprised of ethylene oxide units. Polyethylene glycol-based prepolymers are particularly preferred. The polyols should have a hydroxyl functionality of about 2 or greater, preferably from about 2 to about 6. A wide variety of polyether polyols and polyester polyols may be used. Among the polyether polyols which may be so used are those prepared by reaction of an alkylene oxide with an initiator containing active hydrogen groups, a typical example of the initiator being a polyhydric alcohol (such as ethylene glycol), polyamines (such as ethylene diamine), phosphoric acid, etc. Examples of alkylene oxides which may be employed in the synthesis include ethylene oxide, propylene oxide, any of the isomeric butylene oxides, and mixtures of two or more different alkylene oxides such as mixtures of ethylene and propylene oxide. The resulting polymers contain a polyether backbone and are terminated by hydroxyl groups. Examples of polyhydric alcohols which may be reacted with alkylene oxides to produce useful polyether polyols include, but are not limited to:
propylene glycol
trimethylene glycol
1,2-butylene glycol
1,3-butanediol
1,4-butanediol
1,5-pentanediol
1,2-hexylene glycol
1,10-decanediol
1,2-cyclohexanediol
2-butene-1,4-diol
3-cyclohexene-1,1-dimethanol
diethylene glycol
(2-hydroxyethoxyl)-1-propanol
4-(2-hydroxyethoxy)-1-butanol
2-allyloxymethyl-2-methyl-1,3-propanediol
thiodiglycol
1,2,6-hexanetriol
1,1,1-trimethylolpropane
3-(2-hydroxyethoxy)-1,2-propanediol
3-(2-hydroxypropoxy)-1,2-propanediol
1,1,1-tris[(2-hydroxyethoxy)methyl]ethane
1,1,1-tris[(2-hydroxypropoxy)methyl]propane
triethanolamine
triisopropanolamine
resorcinol
hydroquinone
catechol
3-hydroxy-2-naphthol
bis-phenols such as 2,2-bis(p-hydroxyphenyl)propane and bis-(p-hydroxyphenyl)methane
1,1,2-tris-(hydroxyphenyl)ethane
1,1,3-tris-(hydroxyphenyl)propane.
Also especially desirable are the polyoxyethylene polyols $HO-(CH_2CH_2O)_{\overline{x}}H$.

The polyester polyols which may be employed as prepolymer precursors are most readily prepared by condensation polymerization of a polyol with a polybasic acid. The polyol and acid reactants are used in proportions such that essentially all the acid groups are esterified and the resulting chain of ester units is terminated by hydroxyl groups. Representative examples of polybasic acids for producing these polymers include:
oxalic acid
malonic acid
succinic acid
glutaric acid
adipic acid
maleic acid
fumaric acid
glutaconic acid
$\alpha$-hydromuconic acid
$\beta$-hydromuconic acid
$\alpha$-butyl-$\alpha$-ethylglutaric acid
$\alpha,\beta$-diethylsuccinic acid
ophthalic acid
isophthalic acid
terephthalic acid
citric acid
benzenepentacarboxylic acid
1,4-cyclohexane dicarboxylic acid
diglycollic acid
thiodiglycollic acid
dimerized oleic acid
dimerized linoleic acid
and the like. Representative examples of polyols for forming these precursors include:
ethylene glycol
1,3-propylene glycol
1,2-propylene glycol
1,4-butylene glycol
butene-1,4 diol
1,5-pentane diol
1,4-pentane diol
1,6-hexane diol diethylene glycol
glycerine
trimethylol propane
1,3,6-hexanetriol
trimethanolamine
pentaerythritol
sorbitol,
and any of the other polyols listed above in connection with the preparation of polyether polyols.

The polyol is end capped with an aliphatic or aromatic polyisocyanate. Suitable polyisocyanates include, but are not limited to:
toluene-2,4-diisocyanate
toluene-2,6-diisocyanate
commercial mixtures of toluene-2,4 and 2,6-diisocyanates
isophorone diisocyanate
ethylene diisocyanate
ethylidene diisocyanate
propylene-1,2-diisocyanate
cyclohexylene-1,2-diisocyanate
cyclohexylene-1,4-diisocyanate
m-phenylene diisocyanate
3,3'-diphenyl-4,4'-biphenylene diisocyanate
3,3'-dichloro-4,4'-biphenylene diisocyanate
1,6-hexamethylene diisocyanate
1,4-tetramethylene-diisocyanate
cumene-2,4-diisocyanate
4-methoxy-1,3-phenylene diisocyanate
4-bromo-1,3-phenylene diisocyanate
2,4-dimethyl-1,3-phenylene diisocyante
2,4-diisocyanatodiphenylether
4,4'-diisocyanatodiphenylether
benzidinediisocyanate
4,6-dimethyl-1,3-phenylene diisocyanate
9,10-anthracene diisocyanate
4,4'-diisocyanatodibenzyl
3,3'-dimethyl-4,4'-diisocyanatodiphenylmethane
2,4-diisocyanatostilbene
1,4-anthracenediisocyanate
2,5-fluorenediisocyanate
1,8-naphthalene diisocyanate
2,6-diisocyanatobenzfuran
2,4,6-toluene triisocyanate
p,p',p''-triphenylmethane triisocyanate.

The end capping reaction may be by any convenient method or procedure. For example, the reaction may be conducted in an inert moisture-free environment, such as under a nitrogen blanket, at atmospheric pressure and at temperatures in the range of about 0° C. to about 120° C. For additional specific examples of prepolymers useful in this invention, reference may be made to U.S. Pat. No. 4,137,200 (Wood et al.), the teachings of which are incorporated herein by reference. This invention, however, is not limited to use of the prepolymers described in that patent.

The untreated support matrix is contacted with the prepolymer in a volatile organic solvent. Any solvent which is nonreactive with the support matrix and with the isocyanate groups of the prepolymer will be suitable. Acetone is particularly suitable. Alcohols and chlorinated hydrocarbons may be used. The concentration of prepolymer should be about 0.1 to about 20.0 percent, preferably about 0.1 to about 7.5 percent. The support matrix and prepolymer solution should remain in contact for at least about one minute, preferably about five to ten minutes, and most preferably at least thirty to sixty minutes.

It may be desirable to use a surfactant in preparing the prepolymer solution. Non-ionic surfactants or detergents such as Tween-20 or Tween-80 (TM, ICI United States) or Triton X100 (TM, Rohm & Haas Co.) are suitable and may be used in concentrations of about 0.01 to about 1.0%.

The prepolymer-treated support matrix is then dried. It is preferred to air dry at ambient temperatures. However, drying may be conducted at higher or lower temperatures, if desired. Drying under vacuum conditions also will be suitable. Drying for about one to about 24 hours normally will be sufficient although longer or shorter times may be suitable for some drying conditions.

The desired bioaffinity agent then is applied to the treated support matrix. This agent most typically will be an antibody to the target protein, most preferably a monoclonal antibody. In preparing the improved assay supports of this invention, only minor amounts of the biologically active agent need to be applied to the polymer-treated support matrix. For example, in an embodiment utilizing a treated microporous membrane, the active agent may be dotted onto the membrane in quantities at least as low as about 1.0 microgram per assay, i.e., about 1.0 microliter of a 1.0 milligram per milliliter solution of the bioaffinity agent. The agent may be used in quantities of about 0.01 to about 10.0 micrograms. This compares quite favorably with conventional methods which typically require one to two orders of magnitude more of the biologically active agent, that is, about 10 to 100 micrograms per asssy. In an embodiment utilizing a treated particulate matrix, the biologically active agent may be applied by soaking, spraying or other convenient means. In an embodiment using a device such as a microliter plate, the biologically active agent may be deposited in any convenient manner, for example by spraying, etc.

The support matrix is then dried thoroughly to fix the biologically active agent onto its surface. Air drying at ambient temperatures is preferred. As above, drying at other temperatures or under vacuum conditions will be suitable, provided that the conditions do not denature the bioaffinity agent. Thorough drying is necessary to adequately immobilize the bioaffinity agent. Typical times range from about fifteen minutes to about 30 hours or more. For purposes of this description, the matrix which has been treated with polymer and onto which a bioaffinity agent has been immobilized will be referred to as an "assay support" or "assay support matrix."

Permanent, covalent attachment of the bioaffinity agent to the support matrix probably is not achieved by this process. However, immobilization of the bioaffinity agent onto the support is sufficient for the uses contemplated by this invention. Dissolution and removal of the bioaffinity agent from the support requires washing for longer periods and/or under harsher conditions than typically encountered during diagnostic assay procedures, which have been briefly summarized above. For example, the support will be serially contacted with the test fluid and the recognition conjugate and substrate solutions, with simple rinsing steps in-between. It has been demonstrated that sufficient quantities of the bioaffinity agent remains immobilized on the assay support matrix during these steps to yield a reliable assay support matrix with good sensitivity.

In an alternative embodiment, permanent covalent attachment of the bioaffinity agent to the support matrix may be achieved. The antibody or other agent may be bound to the polymer-treated support matrix by the addition of a crosslinking agent. Amine crosslinking agents such as glutaraldehyde react with the amine groups of the bioaffinity agent and the amine groups of the polymer surface and will be suitable for this purpose. Other suitable amine crosslinking agents include di- or trifunctional amine reactive agents such as diepoxides, di- or triisocyanates, disuccinimidyl suberate or dimethyl suberimidate and the like. Alternatively, the amino groups on the polymer surface can be attached to the carboxylate groups of the bioaffinity agent using crosslinking agents such as carbodiimides or carbonyldiimidazoles, for example. The crosslinking agent may be added before, with or after application of the bioaffinity agent. This embodiment will be particularly useful in those applications where it is desired that the bioaffinity agent be more tightly bound to the assay support matrix.

Assay support matrices prepared according to this invention may be used to test fluids for the presence of a particular target protein. For example, bodily fluids such as urine, plasma, serum or whole blood may be tested. The bioaffinity agent is sufficiently immobilized on the support matrix to resist displacement by other proteins during assay. This is true even where test fluids such as blood or blood components are used, which contain significant quantities of background protein in addition to the target protein. These assay support matrices also may be used to test for the presence of proteins in other types of fluids, for analytical purposes other than diagnosis.

Moreover, the assay support matrices of this invention may be used directly following immobilization of the bioaffinity agent. The need for a protein blocking step has been eliminated. The assay matrices of this invention are not susceptible to nonspecific protein binding, so long as the matrix remains wet or in an aqueous state. That is, only the target protein will be bound to the support matrix during the assay, and the binding will occur only in the area of the immobilized bioaffinity agent by virtue of the unique binding sites associated therewith. Thus, interference from other proteins present in the test fluid has been eliminated, as has possible ambiguity of test results caused by indiscriminate binding of the target protein.

The assay support matrix of this invention may be used according to conventional assay methods and procedures. In the embodiment utilizing a microporous membrane treated as described above, the test fluid typically will be passed through the assay support membrane, preferably followed by rinsing. Next, a solution of an appropriate recognition conjugate is passed through the membrane, again preferably followed by rinsing. Finally, a substrate solution is passed through the membrane which will cause a color change in the area of the bound bioaffinity agent/target protein/recognition conjugate complex. The appearance of this color change indicates the assay is positive for the target protein; lack of color change indicates the absence of the target protein in the test fluid. Using the assay support of this invention, a color change may be apparent within about 10.0 to about 20.0 seconds. Other procedures and variations for using the immobilized bioaffinity agent membrane of this invention may be used as desired.

Particulate assay matrices prepared according to this invention may be used in a similar manner, that is, by sequentially passing the test and reagent solutions through a bed containing the assay matrix and observing the presence or absence of a color change. Alternatively, the particulate assay matrix may be added batchwise to the test fluid, removed by filtration or other means, then added to the reagent solutions in a similar manner. Any convenient method of contacting the assay matrix with the test fluid and reagent solutions will be suitable.

The above description is written in terms of a colorimetric assay, in which the recognition conjugate comprises an enzyme such as horseradish peroxidase which cause a visually apparent color change under positive test conditions. The utility of the assay support matrices of this invention is not limited to colorimetric assays. These assay matrices may be used with any convenient indicator system. For example, the recognition antibody may be radiolabeled for use in a radioimmunoassay. The examples which follow are given for illustrative purposes and are not meant to limit the invention described herein. The following abbreviations have been used throughout in describing the invention.

C—degrees Centigrade
meq—milliequivalent(s)
mg—milligram(s)
mIU—milli-International Unit(s)
ml—milliliter(s)
mm—millimeters(s)
MW—molecular weight
$\mu$l —microliter
PBS—phosphate buffered saline
%—percent

EXAMPLE I

A microporous nylon Magna (TM, Micron Separations Inc.) membrane was placed in a 1.0% solution of HYPOL 3100 (TM, W. R. Grace & Co.) in acetone containing 0.1% Tween-20 (TM, ICI United States, Inc.) for 60 minutes. The membrane was removed from the solution, allowed to drip dry and then air dried at room temperature for 18 hours. Monoclonal antibody to $\beta$-HCG (a protein found in the blood and urine of pregnant women) was applied (1.0 $\mu$l of a 1.0 mg/ml solution in buffer (PBS) to the center of each membrane disc. The discs were allowed to air dry at room temperature for 18 hours.

EXAMPLE II

A 25 mm diameter membrane disc as prepared in Example I was placed in a plastic holder over a nonwoven, hydrophobic polypropylene disc which in turn was placed on an absorbent pad. Good contact between the discs and the absorbent pad was maintained during the assay. Sample $\beta$-HCG-spiked urine (containing 25 mIU $\beta$-HCG in 1.0 ml) was applied in a volume of 200 $\mu$l to the center of the membrane surface and allowed to flow through the membrane under capillary action. A control was run using a membrane from Example I, to which was added a similar amount of urine which did not contain the $\beta$-HCG protein.

Recognition antibody-enzyme conjugate (150 $\mu$l) comprising a recognition antibody to $\mu$-HCG coupled to the enzyme horseradish peroxidase was added to each membrane and allowed to flow through. The membranes were washed with buffer (PBS containing 0.05% Tween-20 (TM, ICI United States, Inc.)) by adding 1.5 ml buffer to the holder and allowing it to flow through the membrane.

Enzyme substrate solution comprising tetramethyl benzidine and peroxide in an acetate buffer was added to the surface of the membranes and allowed to react for two minutes. The membranes were examined for the presence of a color cange. On the membrane receiving β-HCG-spiked urine, a blue dot was observed in the center of the otherwise white membrane, indicating a positive result. The control membrane remained completely white, with no visible color change.

EXAMPLE III

The assay procedure of Example II was repeated, using β-HCG-spiked blood plasma (containing 25 mIU β-HCG in 1.0 ml) instead of urine. The results were the same as described in Example II.

EXAMPLE IV

Membranes were prepared according to procedures of Example I, except as noted here. The nylon membrane was placed in a 2.0% solution (in acetone) of a prepolymer prepared as follows:

TPEG10000 (TM, Union Carbide Corp.) a triol of 10,000 MW composed of 100% ethylene oxide monomer, was deionized using Britesorb 90 (TM, Philadelphia Quartz Co.) (2% of polyol weight suspended in an equal weight of water), by heating in the presence of toluene (800.0 ml per kilogram of the polyol) at 93.0° C. for 2.5 hours, then filtering over a bed of Celite (TM, Jons-Manville Products Corp.) while still hot. The solvent was removed by flash evaporation andrresidual water stripped at 110° C. for 4.0 hours at 1.0–2.0 mm Hg. All glassware was washed with sulfuric acid, rinsed thoroughly with deionized water and dried.

Following this deionzation procedure, 300.0 gm TPEG10000 was mixed with 22.0 gm isophorone diisocyanate (IDPI) and 0.16 gm Santonox R (TM, Monsanto Industrial Chemicals Co.) and heated a 70° C. under dry nitrogen until isocyanate values reached 0.36 meq/gm (theoretical=0.28 meq/gm). Isocyanate levels were determined by addition of dibutylamine and back titration with standard acid.

The prepolymer was used as a 30% solution of DMF (dimethyl formamide). No Tween-20 was used with this prepolymer. The discs were otherwise prepared as in Example I.

EXAMPLE V

The assay procedure of Example II was repeated, using the discs prepared in Example IV. The results were the same as described in Example II.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

We claim:

1. An assay support matrix for an immobilized biologicals assay comprising a support matrix which consists of a microporous membrane or particulate media having a protein non-adsorptive polyurethane polymeric coating thereon, with a bioaffinity agent immobilized on said polymeric coating by passive adsorption.

2. The assay support matrix of claim 1 in which said microporous membrane is nylon, polypropylene, polyester, polyvinyl fluoride, Teflon or cellulsose.

3. The assay support matrix of claim 1 in which said particulate media is silica gel or an inorganic or organic beaded matrix.

4. The assay support matrix of claim 1 in which said polyurethane polymer is one formed by polymerization of a prepolymer prepared by capping a polyoxyalkylene polyol with a polyisocyanate compound, said prepolymer having a reaction functionality greater than two.

5. The assay support matrix of claim 4 in which said polyoxyalkylene polyol is a polyethe polyol or a polyester polyol.

6. The assay support matrix of claim 4 in which said prepolymer is a polyethylene glycol-based prepolymer.

7. The assay support matrix of claim 1 in which said bioaffinity agent is an antibody.

8. The assay support matrix of claim 7 in which said antibody is a monoclonal antibody.

9. A method for preparing an assay support matrix for an immobilized biologicals assay comprising:
(a) selecting a support matrix which is a microporous membrane or particulate media,
(b) coating said support matrix with a solution comprising a polyurethane prepolymer and a volatile organic solvent,
(c) drying the coated support matrix of step (b) to render said support matrix substantially protein non-adsorptive,
(d) applying to the dried, coated support matrix a solution comprising a bioaffinity agent, and
(e) thoroughly drying the support matrix of step (d) to immobilize said bioaffinity agent on said coated support matrix by passive adsorption.

10. The method of claim 9 in which the selected support matrix is a microporous membrane of nylon, polypropylene, polyester, polyvinyl fluoride, Teflon or cellulose.

11. The method of claim 9 in which said volatile organic solvent is selected from acetone, alcohols and chlorinated hydrocarbons.

12. The method of claim 9 in which said polyurethane prepolymer is one prepared by capping a polyoxyalkylene polyol with a polyisocyanate compound, said prepolymer having a reaction functionality greater than two.

13. The method of claim 12 in which said polyoxyalkylene polyol is a polyether polyol or a polyester polyol.

14. The method of claim 12 in which said prepolymer is a polyethylene glycol-based prepolymer.

15. The method of claim 12 in which the concentration of prepolymer in the solution of step (b) is about 0.1 to about 20.0 percent.

16. The method of claim 15 in which said concentration is about 0.1 to about 7.5 percent.

17. The method of claim 9 in which the solution of step (b) also comprises a non-ionic surfactant.

18. A diagnostic assay system comprising an assay support matrix which consists of a microporous membrane or particulate media having a protein non-adsorptive polyurethane polymer coated thereon and a bioaffinity agent immobilized on said polymer by passive adsorption, and further comprising a holder for said assay support matrix.

19. The diagnostic assay system of claim 18 in which said polyurethane polymer is one formed by polymerization of a prepolymer prepared by capping a polyoxylakylene polyol with a polyisocyanate compound, said prepolymer having a reaction functionality greater than two.

20. The diagnostic assay system of claim 19 in which said prepolymer is a polyethylene glycol-based prepolymer.

* * * * *

UNITED STATES PATENT AND TRADEMARK OFFICE
CERTIFICATE OF CORRECTION

PATENT NO. : 4,794,090

DATED : December 27, 1988

INVENTOR(S) : Marc E. Parham and Julie L. Rudolph

It is certified that error appears in the above-identified patent and that said Letters Patent is hereby corrected as shown below:

Col. 8, line 62 : "µ-HCG" should be --β-HCG--.
Col. 9, line 18 : "prccedures" should be --procedures--.
Col. 9, line 30 : "andrresidual" should be --and residual--.

Claim 2, Col. 9, line 68: "celluslose." should be --cellulose.--.

Claim 5, Col. 10, line 10: "polyethe" should be --polyether--.

Signed and Sealed this

Twenty-third Day of May, 1989

Attest:

DONALD J. QUIGG

Attesting Officer

Commissioner of Patents and Trademarks